Figure 1:
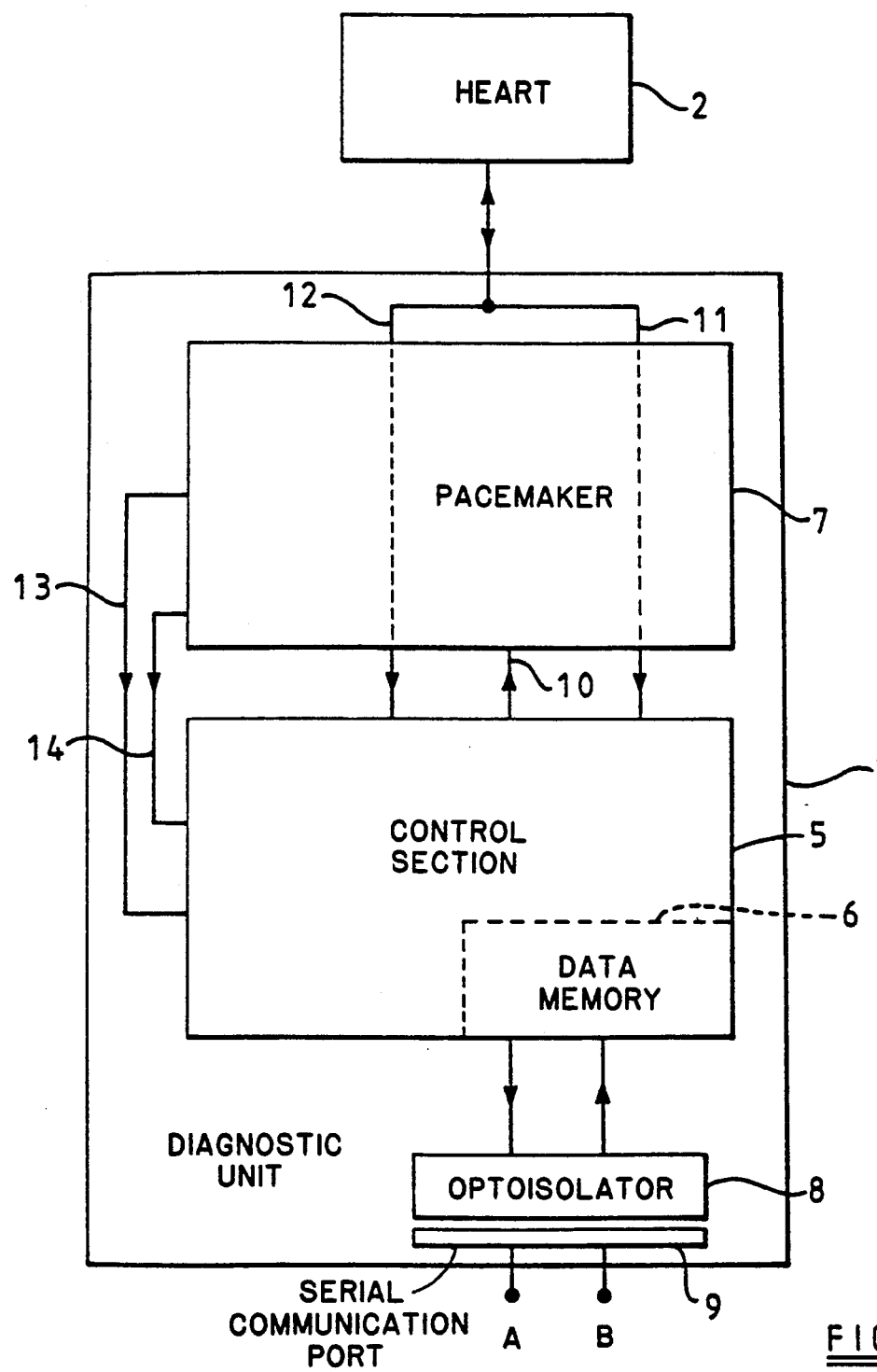

United States Patent [19]
Baker et al.

[11] Patent Number: 5,261,401
[45] Date of Patent: Nov. 16, 1993

[54] AMBULATORY CARDIAC DIAGNOSTIC UNITS HAVING MEANS FOR INHIBITING PACEMAKER RESPONSE

[76] Inventors: James Baker; John M. Horwood, both of University of Exeter; David J. Woollons, Royal Devon & Exeter Hospital; Nicola L. Prosser, University of Exeter; David B. Shaw; Anthony W. T. Whistance, both of Royal Devon and Exeter Hospital, all of Exeter, England

[21] Appl. No.: 681,540
[22] PCT Filed: Nov. 3, 1989
[86] PCT No.: PCT/GB89/01315
§ 371 Date: Jun. 27, 1991
§ 102(e) Date: Jun. 27, 1991
[87] PCT Pub. No.: WO90/04942
PCT Pub. Date: May 17, 1990

[30] Foreign Application Priority Data
Nov. 4, 1988 [GB] United Kingdom ............ 8825800

[51] Int. Cl.$^5$ .............................................. A61N 1/37
[52] U.S. Cl. ...................................... 607/9; 128/696; 128/710
[58] Field of Search ............... 128/419 PG, 419 PT, 128/710, 696, 697, 702, 419 D

[56] References Cited

U.S. PATENT DOCUMENTS

| | | | |
|---|---|---|---|
| 3,614,954 | 10/1971 | Mirowski et al. | 128/419 D |
| 3,805,795 | 4/1974 | Denniston et al. | 128/419 D |
| 4,223,678 | 9/1980 | Langer et al. | 128/419 D |
| 4,250,888 | 2/1981 | Grosskopf . | |
| 4,295,474 | 10/1981 | Fischell | 128/419 D |
| 4,305,396 | 12/1981 | Wittkampf et al. | 128/419 PG |
| 4,407,288 | 10/1983 | Langer et al. | 128/419 PG |
| 4,513,743 | 4/1985 | van Arragon et al. | 128/419 PG |
| 4,523,595 | 6/1985 | Zibell | 128/419 D |
| 4,552,154 | 11/1985 | Hartlaub . | |
| 4,625,730 | 12/1986 | Fountain et al. | 128/419 D |
| 4,913,146 | 4/1990 | DeCote, Jr. | 128/419 PG |
| 5,012,411 | 4/1991 | Policastro et al. | 128/710 |
| 5,012,814 | 5/1991 | Mills et al. | 128/697 |
| 5,088,488 | 2/1992 | Markowitz et al. | 128/419 PG |

FOREIGN PATENT DOCUMENTS
0212278 3/1987 European Pat. Off. .

OTHER PUBLICATIONS

"Design, Implementation and Evaluation of a Microcomputer-based Portable Arryhythmia Monitor", *Medical & Biological Engineering & Computing*, vol. 22, No. 2, Mar. 1984, by N. V. Thakor et al.

"The Use of a Microprocessor-controlled Multichannel Analyser in Transferring Blood Pressures and Neural Activities to Offline Computer Analysis", *Medical & Biological Engineering & Computing*, vol. 18, No. 3, May 1980, by S. J. Hyodynmaa et al.

*Primary Examiner*—William E. Kamm
*Assistant Examiner*—Kennedy J. Schaetzle
*Attorney, Agent, or Firm*—Young & Thompson

[57] ABSTRACT

The diagnostic unit 1 consists of a microprocessor-based control section 5, a data memory 6 and a pacemaker 7. The control section 5 monitors heart action using the intracardiac electrogram and a second signal representative of intracardiac pressure. It detects events of interest to clinicians including bradycardia, tachycardia, cardiac pauses, pressure pauses, interference and pacing pauses, and records the numbers of each type of event. Selective recordings of the waveforms of the sensed signals are made in memory within the unit whenever an event of interest is detected. The unit is worn by the patient for periods of up to three weeks, and the parameters of the events to be sensed can be programmed into the unit by the clinician using a computer 4. The same computer 4 is used to extract and display the recorded data.

10 Claims, 2 Drawing Sheets

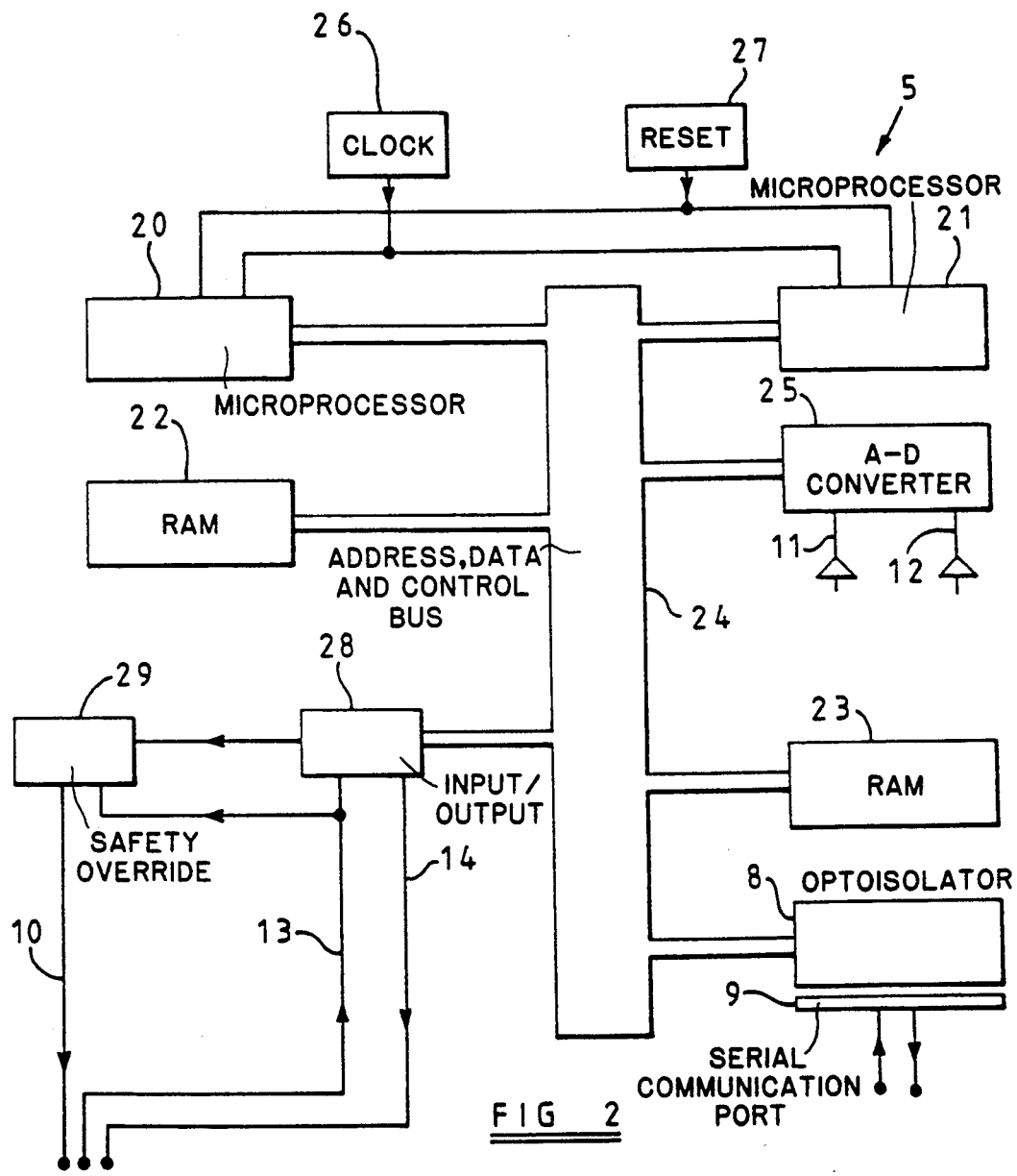

AMBULATORY CARDIAC DIAGNOSTIC UNITS HAVING MEANS FOR INHIBITING PACEMAKER RESPONSE

This invention relates to ambulatory cardiac diagnostic units, that is to units which may be worn by a patient and which serve to monitor the patient's heart with a view to providing data which may be used to diagnose heart malfunction.

It is known for patients having certain heart disorders to be fitted with a pacemaker which may be implanted by surgery and which provides electrical outputs for pacing beating of the heart. It is also known to monitor the electrocardiogram of a patient over a the period of a day by using a 24-hour tape loop recording device which may be worn by the user (N. J. Holter, "New Method for Heart Studies: Continuous Electrocardiography of Active Subjects", Science 134:1214, 1961).

However, the shortcomings of such Holter monitoring has been apparent in many clinical situations for some time, and there has been a need for some form of recording pacemaker. The demand for such a recording pacemaker would be considerable, particularly for the diagnosis of heart disease causing infrequent disturbances and unexplained syncope (D. B. Shaw, C. A. Kekwick, D. Veale, T. W. Whistance, "Unexplained Syncope", Pace July 6, 1983). Current data emphasises the difficulty in diagnosis of heart disease under such conditions, even after complex studies in hospital. Most pacing centres which do not have a special interest in sinus node disease do not have the time or facilities to undertake prolonged investigations. In the absence of any clear evidence of any major sinus node function disturbance the patient's symptoms are commonly labelled as "non-cardiac". However the following publications suggest that further follow-up investigations would indicate that potential benefit would result from pacing with an appropriate unit: R. A. Winkle "Long-term electrocardiographic and event recorders for the diagnosis and treatment of cardiac arrhythmias", Circulation (Supplement) 75: III-53, 1987; J. T. Bigger "Perspectives on long-term recording and monitoring", Circulation (Supplement) 75: III-58, 1987; D. B. Shaw, T. W. Whistance, "Clever Pacemakers", Hospital Update, November 1986. U.S. Pat. Nos. 4,183,354, 4,250,888, 4,363,397 and 4,513,743 disclose various forms of diagnostic recorder but none of these matches the criteria which are believed to be of importance in providing satisfactory diagnosis under a variety of conditions.

It is an object of the invention to provide a generally improved form of ambulatory cardiac diagnostic unit.

According to the present invention there is provided an ambulatory cardiac diagnostic unit comprising recording means for recording data indicative of cardiac function for subsequent analysis, the recording means being adapted to record data representative of electrical activity of the heart measured over a cardiac event monitoring period, and control means for controlling recording over said cardiac event monitoring period in response to sensing of a cardiac event, characterised in that the unit further comprises pacing means adapted to initiate pacing of the heart under control of said control means such that following sensing of a heart malfunctiuon pacing of the heart is initiated after recording of data indicative of a cardiac event has taken place over said cardiac event monitoring period.

Preferably the control means is adapted to control the pacing means so as to give demand pacing for a predetermined duration following said cardiac event monitoring period.

The recording means may also be adapted to record data indicative of a second cardiac function, such as intracardiac pressure (or rate of change of pressure) or intracardiac impedance.

Preferably both signals are used in combination to provide reliable detection of heartbeats. Furthermore the unit may be adapted to detect whether "capture" has occurred during pacing.

Conveniently the signals are sensed using a single intracardiac catheter. Furthermore the unit may be adapted to measure the interval between sensed beats, and optionally to store a histogram of the time intervals between successive beats. This time interval may be used to detect bradycardia or tachycardia. Furthermore the time interval may be used to detect a pause in pressure beats.

Additionally the unit may be adapted to measure the duration since the last detected heartbeat, for example so as to detect asystole. Furthermore the sensed signals may be used to detect electrical interference.

The unit may be adapted to initiate pacing in response to prolonged bradycardia, pause events or interference.

In order that the invention may be more fully understood, a preferred embodiment of the invention will now be described, by way of example, with reference to the accompanying drawings, in which:

FIG. 1 shows an overall block diagram of the unit;
FIG. 2 shows a block diagram of a control section of the unit.

The ambulatory cardiac diagnostic unit which will now be described with reference to the drawings is intended to simultaneously measure, process and selectively record both a first signal being the intracardiac electrogram and a second signal representative of intracardiac pressure. The unit also detects and records certain defined cardiac events for subsequent playback. The unit may be worn externally by the patient for relatively short periods, for example of up to three weeks, although the eventual objective is an implantable device which may be worn indefinitely.

The cardiac events which are detectable by the unit may be defined as follows:

Bradycardia Event - Bradycardia is said to occur if the average heartrate over 1-8 interbeat periods (programmable) is at or below a certain heartrate. The heartrate at which bradycardia is detected is programmable in the range of 25-45 bpm.

Pause on the Intracardiac Electrogram Channel - A pause is said to occur on the electrical channel if a heartbeat is not detected for a certain length of time. The minimum time span for the definition of a pause is programmable.

Pacing Pause - It is known that on occasions the heart does not beat although it has been paced by a pacemaker (i.e. capture has not occurred). This event will be called a pacing pause.

Tachycardia Event - Tachycardia is said to exist when the average heartrate over a selected number of interbeat periods (3-20) is at or above the selected heartrate (100-200 bpm). Both the number of interbeat periods and the selected heartrate are programmable.

End of Tachycardia - The end of tachycardia is defined such that the heartrate must remain below the selected heartrate for a preset number of consecutive interbeat periods. The number of interbeat periods can also be set between 3 and 20. Consecutive beats are used instead of averaging over a certain number of beats (as with the detection of the start of tachycardia). This ensures that if the heartrate is very near the rate for tachycardia and drifts above and below it, there is less chance of filling up the memory allocated for tachycardia with separate portions of the same tachycardia.

Pressure Pause - A pressure pause is defined as the occurrence of an electrical heartbeat without a corresponding pressure beat. In practice an electrical beat from a contraction of the heart is detected before the corresponding pressure beat. Therefore for detection a pressure pause is defined as two consecutive electrical beats without a pressure beat between them.

Interference - The detection of interference on the electrical channel relies on the detection of interference spikes. These spikes must pass an amplitude threshold and occur at greater than a preset frequency. The amplitude threshold programmable and the minimum frequency for interference is 10 Hz.

FIG. 1 shows the diagnostic unit 1 connected by leads to the heart 2. It also shows a hand-held battery operated key 3 and a computer 4 to which the unit 1 may be selectively connected. Parameters are transferred from the computer 4 to the diagnostic unit 1 prior to connecting the diagnostic unit 1 to the transducer catheter (not shown), that is to the patient's heart. The computer 4 is disconnected from the diagnostic unit 1 before the unit 1 is attached to the catheter. Monitoring is then started by sending a signal to the unit 1 from the hand-held key 3 which is temporarily connected to the unit 1 for this purpose. The same key 3 is also used to stop monitoring prior to extraction of the recorded data from the unit 1 to the computer 4.

The diagnostic unit 1 consists of a control section 5, a data memory 6 forming part of the control section 5, and an adapted commercial pacemaker 7, together with transducers and batteries (not shown). Optoisolators 8 are used to provide electrical isolation of the serial communication port 9. The terminals A and B of the port 9 may be connected either to the terminals A', B' of the computer 4 or to the terminals A", B" of the key 3.

The pacemaker 7 used is a demand pacemaker, that is it only paces if the time from a spontaneous beat before a further spontaneous beat is detected exceeds a preset time. The pacemaker 7 is partially controlled by the control section 5 in that the timing mechanism (or clock) of the pacemaker 7 can be switched on or off by the control section 5 by means of a clock on/off signal line 10. While the clock is switched on pacing can occur, but pacing cannot occur while the clock is switched off. Detection of intracardiac electrogram beats is carried out by the pacemaker 7 regardless of whether the clock is on or off.

An intracardiac electrogram signal is supplied both to the pacemaker 7 and to the control section 5 by a signal line 11, and a second heart signal representative of intracardiac pressure is supplied by a signal line 12. The control section 5 detects intracardiac electrogram beats independently of the pacemaker 7 so as to allow pacing pauses to be detected. When a spontaneous beat is detected by the pacemaker 7 it sends a signal to the control section 5 by way of a sense signal line 13. Furthermore the pacemaker 7 also sends a signal to the control section 5 by way of a pace initiate signal line 14 when a pacing pulse is generated. These signals allow interbeat periods to be calculated by the control section 5.

Referring to FIG. 2 the control section 5 comprises two microprocessors 20 and 21 sharing a common memory consisting of an 128 K byte RAM module 22 and a 2 K×8 byte RAM 23, and an address, data and control bus 24. The use of two microprocessors sharing common memory allows the separation of the data acquisition and data processing tasks. The two microprocessors 20 and 21 are a 65C112 and a 65C102. By the use of the techniques described in "A low-cost high performance 64 K shared memory system", J.M.K. Horwood and J. Baker, J. of Microcomputer Applications, 1985, 8 both microcomputers retain full access to all the system memory and input/output devices. Virtually no additional logic is required to facilitate this.

2 K bytes of static RAM are provided for purposes other than recorded data storage. This includes the stacks for both microprocessors. The main data storage is 128 K bytes of static RAM, although provision is made for up to 256 K bytes to allow for system expansion.

In operation the control section 5 continually records the intracardiac electrogram and the second signal indicative of intracardiac pressure. A sampling rate of 400 Hz is used for the intracardiac electrogram, whereas a sampling rate of 100 Hz is used for the second signal. However, in the absence of a detected cardiac event, the recorded data is overwritten by newly recorded data after a predetermined interval of time. In the described embodiment 8 K bytes of data are stored for each recorded waveform, this being equivalent to about sixteen seconds of recording. On detection of a cardiac event the control unit produces a recording which is not subsequently overwritten and which is divided into two parts, that is a part recorded before detection of the event and a part recorded after detection of the event. For example twelve seconds of recording may be carried out before the event for both Bradycardia and intracardiac electrogram pauses, leaving four seconds of recording after the detection of the event. For tachycardia, pressures pauses, pacing pauses and interference, eight seconds of recording are taken before and after the detection of the event. Sixteen such recordings may be made in sixteen memory blocks of the module 22, each of which is of 8 K bytes.

When monitoring begins, the first sample value is stored at the first address of the first memory block, and at the same time a code is stored in a register which indicates which block is to be accessed. A pointer indicates at which memory location the sample value is to be stored, and this pointer is incremented after each sample is stored. When the pointer reaches the end of the first memory block (after about sixteen seconds) it returns to the beginning of this memory block and overwrites the previously recorded data. Thus the memory block always contains the most recent sixteen seconds of recorded waveforms.

When an event waveform is to be recorded on detection of a cardiac event, the value of the pointer is recorded. This gives the address of the start of the event, that is the point at which the event is detected, and the sample values are recorded in the memory block for a further preset number of bytes. A part of the previously recorded data is not overwritten, and this part then constitutes the recording immediately preceding the event.

When the recording of the event is complete, the pointer moves to the start of the next memory block, and this next memory block is then continuously overwritten until the next event waveform is to be recorded. This process is continued until all sixteen event waveforms have been recorded. At this point no further sample values are stored in the memory.

The programmes and fixed data for both microprocessors are contained in a single 32 K byte CMOS EPROM which appears in the address map as two banks of 16 K bytes each of which is only accessed by a single microprocessor.

An analogue to digital convertor 25 is used for the intracardiac electrogram and pressure channels. This convertor 25 may be constituted by a single ADC0844 which incorporates a 4-channel multiplexer. The control section 5 also includes a clock unit 26 and a reset unit 27.

Furthermore the connection of the control section 5 to the pacemaker 7 is effected by way of an input/output circuit 28 and a safety override unit 29. In the event of control section failure the safety override unit 29 operates to prevent the clock of the pacemaker remaining off when no spontaneous beats have been detected for longer than a certain length of time.

By way of further explanation of the function of the control mechanism some general definitions of terminology used in this specification will now be given.

Dormant Periods - Dormant periods are introduced for the comfort and safety of the patient. In order to record the waveform of a bradycardia event or a pause on the intracardiac electrogram channel the pacemaker is inhibited for a short time (i.e. it is not allowed to pace). Dormant periods ensure that there is at least a preset time between successive inhibitions of the pacemaker so that unpleasant symptoms that may be experienced by the patient are not allowed to persist.

After the detection of a bradycardia or pause on the electrical channel, the control unit enters a dormant period during which the pacemaker is allowed to function normally. This means that no bradycardia or pause events should occur but monitoring of the other events and updating of the histogram can continue. The dormant period is programmable in the range 0-10 minutes.

There is also a further dormant period which is invoked if more than one bradycardia or pause on the electrical channel is detected within one hour. If more than one of these events does occur in an hour one of two options may be followed. The option to be followed is programmable.

Option 1: The pacemaker is allowed to operate normally for the remaining recording time.

Option 2: The pacemaker is allowed to operate normally for a preset length of time (0-11.5 hours).

The T-wave - The T-wave constitutes that portion of the intracardiac electrogram which immediately follows a beat and is characteristic of the repolarisation of the heart. It is undesirable to pace on the T-wave.

Pacemaker refractory period - Once the pacemaker has detected a beat it enters a short refractory period during which it does not look for the occurrence of a beat. This is to ensure that the T-wave (seen at the end of the beat) is not mistaken for the occurrence of another beat.

The above described diagnostic unit has a number of functions in operation, and these may be summarised as follows:

(i) Monitoring the intracardiac electrogram and second signal using transducers mounted on a catheter positioned in a chamber of the heart.

(ii) Detecting electrical and pressure heartbeats. (Other time varying signals which indicate the function of the heart can be used).

(iii) Detecting and counting events. The events monitored are bradycardia, interference, tachycardia, pressure pauses, pauses on the electrical channel and pacing pauses. Each time one of these events occurs the relevant event counter is updated.

(iv) Allowing variable definitions of the events named above. The exact definitions of the events are set up on the computer and the parameters are transferred to the diagnostic unit prior to the start of monitoring.

(v) Recording the intracardiac electrogram and second signal of sixteen events. The type and time of these events are recorded, as are the times of the start and finish of any tachycardia or interference.

(vi) A histogram of interbeat periods is built up continuously, except when interference is present. There are nine counters with programmable ranges. During interference on the intracardiac electrogram channel monitoring of all other events ceases.

At the start of monitoring or on completion of the dormant periods the pacemaker clock is switched off. This is always done at the end of its refractory period (during which no beats can be detected). The pacemaker clock is always switched on during the dormant periods or on the detection of bradycardia. This is done immediately after the end of a refractory period. The pacemaker is then capable of sensing an intracardiac electrogram beat immediately and there is no chance of missing the detection of a beat or pacing the heart on the T-wave. The clock is also switched on when a pause or interference is detected. In these cases the clock is switched on immediately as there are no spontaneous or paced beats detected. In this case of interference the clock remains on until the end of interference is detected.

The definitions of the events and the recording parameters are set up on the computer prior to the start of monitoring. These parameters are then transferred to the diagnostic unit so that monitoring can commence. The programmable parameters are listed below:

1. The heartrate defining bradycardia.
2. The number of interbeat periods that are averaged in the detection of bradycardia.
3. The duration of time that must elapse from the detection of a spontaneous beat to define the occurrence of a pause.
4. The duration of the dormant period associated with the detection of a bradycardia or intracardiac electrogram pause event.
5. The option for a dormant period associated with the detection of more than one pause or bradycardia in an hour and the duration of the dormant period if the shorter option is chosen.
6. The number of interbeat periods that are averaged in the detection of tachycardia.
7. The heartrate defining tachycardia.
8. The number of interbeat periods that are averaged in the detection of the end of tachycardia.
9. The heartrate defining the end of tachycardia.
10. The ranges of the histogram counters.
11. The number of bradycardia event waveforms that can be recorded.
12. The number of tachycardia event waveforms that can be recorded.
13. The number of intracardiac electrogram pause waveforms that can be recorded.

14. The number of pressure pause waveforms that can be recorded.
15. The number of interference event waveforms that can be recorded.
16. The number of pacing pause waveforms that can be recorded.
17. The number of pressure pause waveforms to be recorded.
18. The signal amplitude threshold for interference.
19. The pressure signal amplitude threshold to define a pressure beat.
20. The duration for which the pressure signal must remain above the amplitude threshold to define a pressure beat.

At the end of monitoring the diagnostic unit is disconnected from the patient and attached to the computer. The recorded data is then transferred from the diagnostic unit to the computer and stored for future reference.

We claim:

1. An ambulatory cardiac diagnostic unit comprising pacing means for pacing the heart, sensing means for sensing electrical activity of the heart, detection means connected to said sensing means for monitoring data outputted by the sensing means which is representative of the electrical activity of the heart and for detecting from said data the occurrence of a heart malfunction, recording means connected to the sensing means and the detection means for recording, in response to detection of a heart malfunction, said data over a cardiac event monitoring period which includes periods both before and after detection of the heart malfunction, and control means for (a) controlling recording by said recording means of said data over said cardiac event monitoring period, and (b) controlling said pacing means so as to inhibit pacing of the heart following detection of a heart malfunction and until recording of said data over said cardiac event monitoring period has been completed by said recording means.

2. An ambulatory cardiac diagnostic unit according to claim 1, wherein said control means is adapted to control said pacing means so as to give demand pacing for a predetermined duration following said cardiac event monitoring period.

3. An ambulatory cardiac diagnostic unit according to claim 1, wherein the recording means is adapted to continuously record data with the previously recorded data being overwritten by newly recorded data after a predetermined interval of time, and the control means is adapted to control recording in response to detection of a heart malfunction so that an initial part of the previously recorded data is overwritten leaving recorded data representative of the electrical activity of the heart over said cardiac event monitoring period.

4. An ambulatory cardiac diagnostic unit according to claim 1, wherein further sensing means are provided for sensing a cardiac function, and the recording means is also adapted to record data indicative of said cardiac function.

5. An ambulatory cardiac diagnostic unit according to claim 4, wherein said cardiac function is intracardiac pressure.

6. An ambulatory cardiac diagnostic unit according to claim 1, wherein the recording means is adapted to record data over a plurality of cardiac event monitoring periods.

7. An ambulatory cardiac diagnostic unit according to claim 1, wherein the detection means is adapted to monitor the interbeat periods between successive heartbeats and to indicate the occurrence of a heart malfunction in response to such monitoring.

8. An ambulatory cardiac diagnostic unit according to claim 1, wherein the detection means is adapted to compare data indicative of monitored heart electrical activity with preset values indicative of acceptable heart performance.

9. An ambulatory cardiac diagnostic unit according to claim 8, wherein the detection means records the number of heart malfunctions detected and their timings.

10. An ambulatory cardiac diagnostic unit according to claim 1, wherein it further comprises interference detection means for inhibiting monitoring in the event of electrical interference.

* * * * *